United States Patent
Ingle et al.

(10) Patent No.: US 6,938,206 B2
(45) Date of Patent: Aug. 30, 2005

(54) SYSTEM AND METHOD FOR CREATING A CLINICAL RESUME

(75) Inventors: David Blakeman Ingle, Austin, TX (US); David James Navin, Williams Bay, WI (US); Dayna Sue Pierzchala, Elmhurst, IL (US); Mark Phillip Snell, Chicago, IL (US)

(73) Assignee: Transolutions, Inc., Lake Bluff, IL (US)

(*) Notice: Subject to any disclaimer, the term of this patent is extended or adjusted under 35 U.S.C. 154(b) by 731 days.

(21) Appl. No.: 09/766,047

(22) Filed: Jan. 19, 2001

(65) Prior Publication Data

US 2002/0138524 A1 Sep. 26, 2002

(51) Int. Cl.$^7$ .............................................. G06F 15/00
(52) U.S. Cl. ..................... 715/530; 715/530; 715/513; 705/2; 705/3; 707/10; 707/102
(58) Field of Search ................. 715/530, 522, 715/503, 505, 512–513, 517; 705/2–3, 51; 707/102, 3, 9–10

(56) References Cited

U.S. PATENT DOCUMENTS

| | | |
|---|---|---|
| 5,331,547 A | 7/1994 | Laszlo |
| 5,508,912 A | 4/1996 | Schneiderman |
| 5,724,580 A * | 3/1998 | Levin et al. ............. 707/104.1 |
| 5,748,907 A * | 5/1998 | Crane ............................ 705/2 |
| 5,823,948 A * | 10/1998 | Ross et al. .................. 600/300 |
| 5,832,470 A | 11/1998 | Morita et al. |
| 5,884,305 A | 3/1999 | Kleinberg |
| 5,903,889 A * | 5/1999 | de la Huerga et al. .......... 707/3 |
| 5,963,952 A | 10/1999 | Smith |
| 5,983,227 A | 11/1999 | Nazem et al. |
| 6,070,158 A | 5/2000 | Kirsch et al. |
| 6,112,202 A | 8/2000 | Kleinberg |
| 6,122,648 A | 9/2000 | Roderick |
| 6,137,488 A | 10/2000 | Kraft et al. |
| 6,226,785 B1 * | 5/2001 | Peterson et al. ............ 717/106 |
| 6,457,018 B1 * | 9/2002 | Rubin ........................... 707/4 |
| 6,473,096 B1 * | 10/2002 | Kobayashi et al. ......... 345/731 |
| 6,535,883 B1 * | 3/2003 | Lee et al. ................... 707/100 |
| 2002/0087356 A1 * | 7/2002 | Andros et al. ................. 705/2 |
| 2002/0128860 A1 * | 9/2002 | Leveque et al. ............... 705/2 |

* cited by examiner

*Primary Examiner*—Joseph Feild
*Assistant Examiner*—Thu V. Huynh
(74) *Attorney, Agent, or Firm*—DLA Piper Rudnick Gray Cary US LLP

(57) ABSTRACT

A system and method are provided for automatically generating a summary document with information mined from a data repository. The database stores information garnered from a plurality of sources. The information includes the type of data which can be easily organized into fields, as well as less definable data such as transcribed dictation. The information is converted into a markup language for parsing and storage as tagged data and marked up data objects. The summary document is created from the tagged and marked up data objects. Specific examples are also provided for the generation of a clinical resume type summary document.

7 Claims, 4 Drawing Sheets

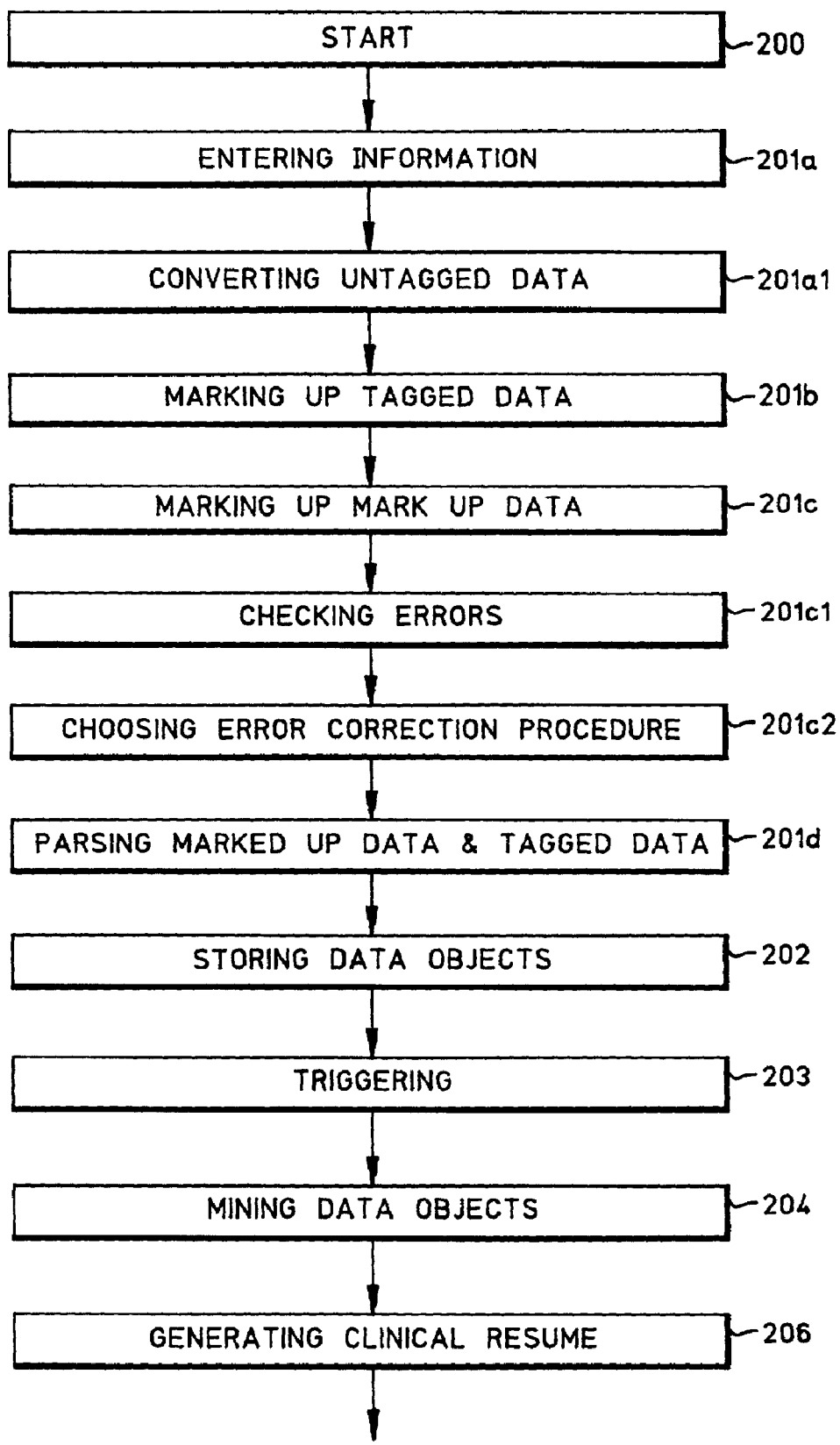

SYSTEM AND METHOD FOR CREATING A CLINICAL RESUME

BACKGROUND OF THE INVENTION

1. Field of the Invention

This invention relates generally to automatic document formulation and, more particularly, to a system and method of creating a clinical resume from mining an electronic database.

2. Description of the Related Art

Traditionally, after a patient is discharged, the physician dictates, or perhaps writes by hand, a clinical resume. A clinical resume can be referred to as a medical discharge summary, a transfer summary, a problem list, or an expiration summary. The clinical resume brings the major elements of a patients care, for each specific visit, into focus in a single document. A medical discharge summary, for example, also provides information for additional teaching, and provides the patient with information needed to care for themselves or get further help. The discharge summary from an acute care facility may serve as a tool for the continuum of care.

A discharge summary is only required after a patient has left the facility, and physicians often view discharge summaries as a background task. The urgent needs of current patients rightfully draw the physician's attention, but facilities incur significant costs because of the resulting delay in generating discharge summaries, completing charts, and billing for and receiving reimbursement. However, the regulations are strict and specific regarding the content and format of all discharge summaries. Non-conformance to regulations can place a facility at risk for losing accreditation.

The Joint Commission on Accreditation of Healthcare Organizations (JCAHO) requires a discharge summary, or clinical resume, whenever a patient is discharged from an accredited facility, as stated in the JCAHO information management (IM) standards IM.7 through IM.7.2. This document must include history and physical information, diagnoses, any recommendations made by the physicians, and other relevant data.

The JCAHO is a quality oversight body for health care organizations and managed care in the United States. In 1965 congress (Health Care Financing Administration—HCFA) passed the Social Security Amendments with a provision that hospitals accredited by the JCAHO, are "deemed" to be in compliance with most of the Medicare Conditions of Participation for Hospitals, and, thus, able to participate in the Medicare and Medicaid programs. The information management (IM) standards IM.7 through IM.7.2 specify that a concise clinical resume included in the medical record at discharge provides important information to other caregivers and facilities continuity of care.

According to JCAHO, the discharge summary is to be completed with 30 days of each patient discharge. However, many facilities have medical staff bylaws written with a much more stringent completion time frame to comply with the following issues: hospital revenue needs with account receivable goals; continuity of patient care; emergency patient transfer; memory accuracy; and, legal implications. Further, the closure of medical records impacts the facilities billing cycle, optical imaging, data abstraction deadlines, computerized data storage, and internal on-line viewing.

The same JCAHO standards require that the discharge summary contains the following information:

reason for hospitalization;
significant findings;
procedures performed and treatment rendered;
patient's condition at discharge; and
instructions to the patient and family, if any.

In addition to the above requirements, the discharge summary usually contains the patients' final diagnoses, treatments and procedures performed during that visit.

In 1997 the JCAHO announced the ORYX program which is expected to be the next evolution in accreditation to integrate the use of outcomes and other performance measures into the accreditation process. This announcement has placed many health care organizations on their toes to assure that their data bases contain all of the JCAHO data requirements for use prior to their next accreditation survey at their facilities.

Congress proposed the Health Insurance Portability and Accountability Act (HIPAA) in 1996, that was passed in 2000. Among other requirements, HIPAA mandated the US Department of Health and Human Services (HHS) to develop a set of regulations concerning the privacy and security of health information. HHS issued recommendations and proposed rules that were published in 1998. They apply to providers, payers, and clearinghouses that handle (either store or transmit) individually identifiable healthcare information. More so than any regulatory drivers to date, the HIPAA security regulations will force healthcare organizations to replace paper-based patient medical records with computer-based patient record systems (CPR's).

An increasing number of health plans are requiring copies of discharge summaries and other pertinent portions of the patient medical record for auditing. Not only Medicare and Medicaid fiscal intermediaries, but healthcare plans of the private sector are increasingly auditing for accurate billing and medical necessity.

Auditors, whether off-site or they come to the facility, are double checking the Health Information Coders to substantiate that each code diagnosis and procedure is actually documented in the patient medical record. They also check legitimate medical necessity for admission to the hospital, and that all drugs and equipment being billed, were ordered by a physician.

According to HIPAA regulations, a hospital may only submit claims for services that the hospital has reason to believe are medically necessary and that were ordered by a physician or other appropriately licensed individual.

The Office of Inspector General (OIG) recognizes that licensed health care professionals must be able to order any services that are appropriate for the treatment of their patients. However, Medicare and other government and private health care plans will only pay for those services that meet appropriate medical necessity standards (in the case of Medicare, i.e., reasonable and necessary services). Providers may not bill for services that do not meet the applicable standards.

The hospital is in a unique position to deliver this information to the health care professionals on its staff. Upon request, a hospital should be able to provide documentation, such as patients' medical records and physicians' orders, to support the medical necessity of a service that the hospital has provided.

It is becoming increasingly desirable to provide a fuller record of the patient's stay in the hospital than is provided in the traditional dictated discharge summary. Preparing a discharge summary involves integrating information extracted from several sources with comments from consulting physicians also responsible for the patient.

Beyond administrative concerns, the discharge summary is the last required documentation to be completed after the patient is discharged from the healthcare facility. This document is important to physicians because it acts to provide:

a summary of the patient's medical and surgical history;

general and emergency continuing care information, such as allergies to medication; poor anesthesia risks; drug interactions; and, present diagnoses being treated;

legal proof of appropriate patient care;

billing for physician services;

patient follow-up instruction for further office visits;

physician practice patterns (by diagnoses and procedures); and physician case load for recertifications.

According to the OIG, every physician who provides or supervises the provision of services to a patient should be responsible for the correct documentation of the services that were rendered. The appropriate documentation must be placed in the patient record and signed by the physician who provided or supervised the provision of services to the patient.

While the importance of the discharge summary to physicians is great, most have difficulty finding time in their busy schedules, with more critical priorities, to complete this documentation. Due to the commitment involved to complete this documentation, many physicians pay to have other staff members dictate the discharge summary for them. The process of generating a discharge summary requires between ten and twenty minutes of the physician's time to read the information and write the discharge information, in addition to the time required to locate and obtain the patient's chart. The summary is in turn transcribed and inserted into the patient's chart like all the other documents generated during their treatment.

This discharge summary is by definition redundant, since every part of a discharge summary is contained in at least one other document. Dictating a discharge summary involves searching through a patient's chart for required and relevant information. A physician can spend about an hour per four or five patients just re-reading previously dictated information. This redundancy, and the overall amount of time involved, often spur physicians or facilities to hire outside labor or other hospital staff to dictate discharge summaries. The savings in physician time comes at the monetary and potential quality cost of using alternative labor.

Computers and software algorithms have been devised to sort and retrieve data, and almost all important medical procedures and events are entered into an electronic database of some sort. However, the medical events are not necessarily stored in the same database. Further, the stored information is not always of a type that is easily retrieved. Predetermined fields, such as name and date of admission are easy to work with, but a significant portion of the medical events are textual diagnosis and observation information that is not necessarily stored by field.

It would be advantageous to automate the preparation of medical discharge summaries, to reduce the amount of physician time and effort required for dictation.

It would be advantageous if an automated discharge summary could be prepared quickly enough that a physician could sign the discharge summary at the same time as the other medical event entrees required to complete and authenticate the record.

It would be advantageous if an automated summary statement could set up to provide a standardized and legible report that makes information easy to find.

It would be advantageous if an automated medical discharge summary could be generated that improved a hospital's position with respect to revenue generation, patient transfers to another facility, legal correspondence, internal on-line viewing, and JCAHO unannounced surveys.

It would be advantageous if all the data necessary to complete a clinical resume could be stored in a data repository for mining. Likewise, it would be advantageous if transcriptions and descriptions, which are difficult to organize by fields, could be stored and mined for use in a clinical resume.

It would be advantageous if a medical summary document could be prepared from source files that have been reviewed, edited, and attested to minimize to amount of human intervention required.

SUMMARY OF THE INVENTION

Accordingly, a method for automatically generating a clinical resume is provided. The method comprises:

transmitting patient documents to a data center via a virtual private network (VPN) or secured direct dial-up connection;

using a multi-pass lexical parser, the documents are broken down by gross structure (such as document sections) and by linguistic structure (such as parts of speech and clinical keywords) and marked up with tags according to a protocol such as HTML, XML, or SGML;

after parsing, a summary generation algorithm operates on the marked up documents, extracting the required sections from each document along with any additional clinical information, for example, diagnoses and irregular lab values; and an assembly algorithm merges the resulting collection of data objects from the marked up documents to create a JCAHO-compliant discharge summary. An output processor renders the marked up documents into a formatted document that meets specified requirements, and the document is returned for review and signature by a user. The process automatically detects irregularities in documentation and alerts a human operator.

A system for automatically generating a clinical resume, and additional details of the above-mentioned process are presented below.

BRIEF DESCRIPTION OF THE DRAWING

FIGS. 2a and 2b are a flowchart illustrating a method for creating a summary document according to the present invention.

DETAILED DESCRIPTION OF THE PREFERRED EMBODIMENTS

Figure 1:
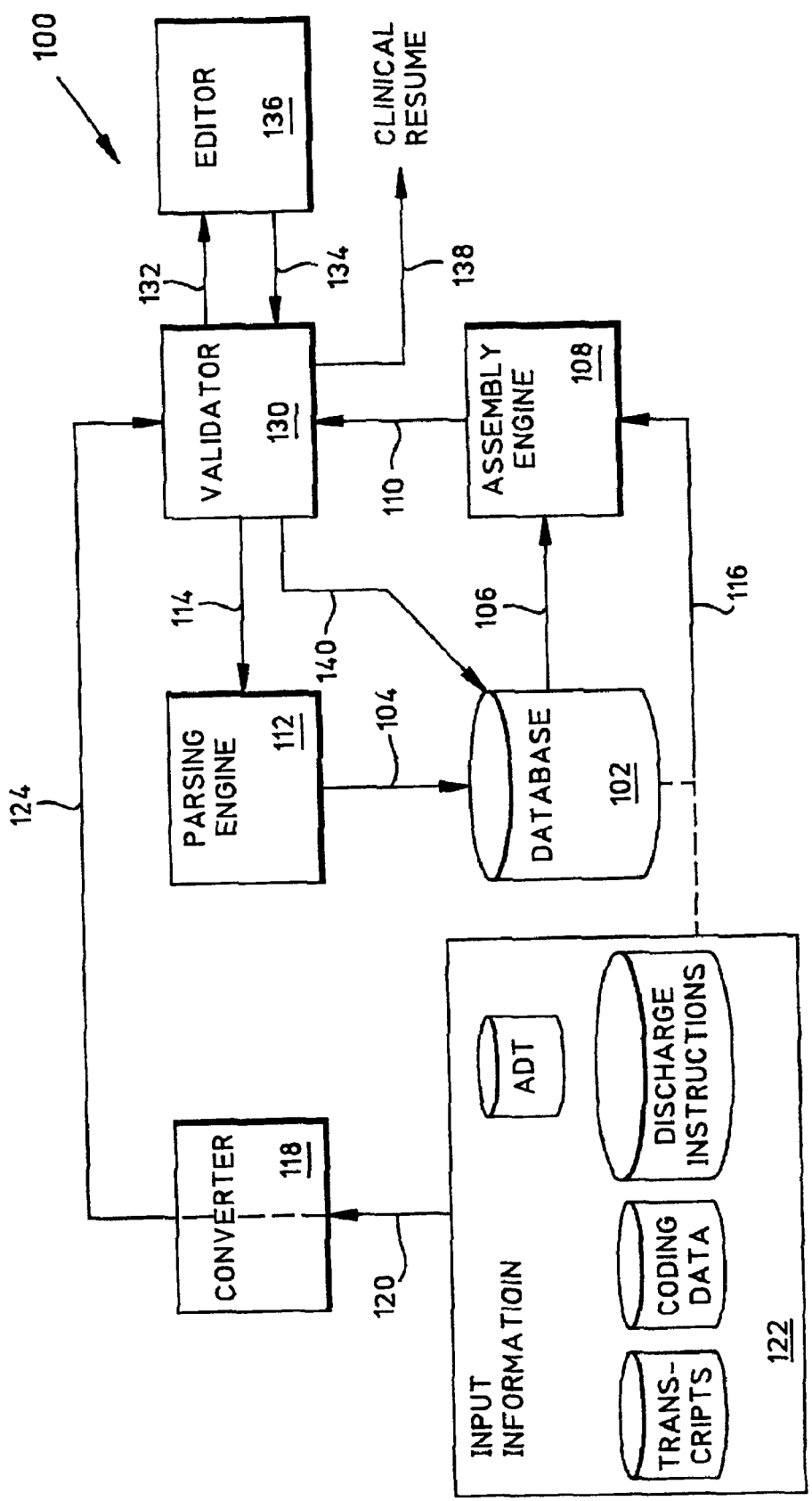
FIG. 1 is a schematic block diagram illustrating the present invention system for creating a summary document from stored data.

FIG. 1 is a schematic block diagram illustrating the present invention system for creating a summary document from stored data. The system 100 comprises a database 102 having an input on line 104 to accept information from a plurality of sources. Although the database 102 is depicted as a single element, it may actual be a data repository that includes many linked databases that provide a uniform front end to the user. The database 102 stores the information in an electronic format as data objects and supplies the data objects at an output on line 106. An assembly engine 108 has a first input connected to the database 102 output on line 106 and an output on line 110 to supply a summary document generated by mining the data objects in the database 102.

The database 102 accepts and stores marked up data objects. Likewise, the assembly engine 108 supplies a summary document by mining the marked up data objects. For example, the database 102 can accept and store physician transcriptions, audio records, and graphical records as marked up data objects.

A parsing engine 112 has an input to accept coding data, discharge instructions, laboratory results, pharmacy records, audio and graphical records, and physician transcription information. The parsing engine 112 marks up and supplies the coding data, discharge instructions, laboratory results, and pharmacy records as tagged data. This type of information is more susceptible to organization and storage as fields. More specifically, the parsing engine 112 accepts coding data, discharge instructions, laboratory results, and pharmacy records selected from the input information group including patient identity fields, account number, worktype ID, job number, transcriptionist ID, dictation date, creation date, facility identity fields, physician identity fields, discharge diagnosis coding fields, procedure coding fields, discharge coding fields, laboratory result fields, and radiation result fields.

In addition, the parsing engine 112 marks up the audio and graphical records, and physician transcriptions as marked up data. This information is by its nature less susceptible to field organization, as its content is less well defined. More specifically, the parsing engine 112 accepts physician transcriptions concerning present illness, history of present illness, impressions on admission, impressions and plans on admission, admitting diagnosis, diagnosis on admission, consultation data, impression and plan at consultation, impression from consultation, and diagnosis from consultation.

With respect to the generation of a medical discharge summary, the parsing engine marks up and stores a plurality of physician transcriptions that are specifically identified under the heading of Reasons for Admission, Impression on Admission, and Consultations. Then, the assembly engine 108 automatically generates a clinical resume with a plurality of Reasons for Admission, Impressions on Admission, and Consultations transcriptions mined from the database 102.

The database 102 stores the tagged data and marked up data as data objects. When required, such as with video data, the database 102 stores the marked up data objects as data binary large objects (BLOBs). The parsing engine 112 marks up the input information into a protocol selected from the group including HTML, XML, SGML, and equivalent protocols. That is, the present invention process will be applicable to developing markup type languages. The assembly engine 108 assembles the pieces of a discharge summary collected by the various collection processes described above. The assembly process results in a relatively large marked up document that may include some superfluous information, parts of documents not to be used in the end discharge summary. When an XML protocol is used, an extensible style sheets transformation (XSLT) script, which can be considered as a component of the assembly engine 108, trims the superfluous data and creates a marked up document formatted for output on line 110. Similar functions are performed with other language protocols.

The assembly engine 108 has an input on line 116 to accept a trigger signal for creating the clinical resume. In response to the trigger signal, the assembly engine 108 generates the clinical resume from the mined data objects automatically within a first number of days of receiving the trigger signal.

Typically the system 100 further comprises a file converter 118 having an input on line 120 to accept input information 122 such as coding data, discharge instructions, laboratory results, pharmacy records, audio and graphical records, and physician transcription information as untagged data. The converter has an output connected to the input of the parsing engine 112 on line 124 to supply the input information 122 in a format suitable for marking up. The input information on line 120 is an electronic format that includes protocols such as delimited HL7, ASCII, and flat-files. However, it is possible to enter the input information in a markup language, so that the information is passed through converter 118 on line 124. The untagged input information 122 can be entered manually, or by machine, and stored in a plurality of databases, as shown. Alternately, the information can be directly submitted, without storage, to the converter 118. The parsing engine 112 marks up the converted input information as tagged data and marked up data.

In some aspects of the invention, the file converter 118 accepts patient admission, discharge date, transfer information, and the attending physician as untagged data in an ADT file and converts the ADT file into a format suitable for marking up. Likewise, the parsing engine 112 marks up the untagged data in the converted ADT file, the database 102 accepts the tagged data and marked up data from the parsing engine 112, and the assembly engine 108 generates a clinical resume with information mined from the ADT file. Generally, the parsing engine 112 matches a patient account number to an ADT record from the ADT data objects in storage.

ADT input information is often supplied in an electronic format such as a fixed-length flat-file format stored in separate directories named for site codes. For simplicity, the FIG. 1 implies that the input information 122 is being supplied from a single site. However, the information is typically collected and initially stored at a plurality of sites before conversion. A directory reader captures and inserts the site code as a property in the envelope. Unlike transcribed documents, the ADT data does not necessarily contain an internal code number for a site.

The converter 118 marks off-length rows with an error marker, and the parsing engine 112 detects instances of the error marker as well as potential issues with content, e.g., patient name string contains numbers. The parsing engine 112 writes information about errors to an validator (presented below), and good data is stored in a table with specific data fields and a marked up document or fragment representing the row.

The ADT table stores at least the following fields as discrete information:

Site code (drawn from the envelope);

Patient name;

Patient MRN;

Patient account number;

Date of admission; and

Date of discharge.

Individual rows of the flat file may contain specific transaction codes that indicate how the row is to be used with respect to the database, e.g., an addition, update, merge, or deletion.

The coding and discharge instruction data collection process mirrors the ADT collection process for files. Files are accepted from a directory keyed for the site, and the resulting data and error information is written to tables in database 102 as discrete data and data BLOBs.

A History and Physical (H&P) is a type of input information, determined by a combination of site and worktype as listed in the document header, that should have content in sections labeled as Reason for Admission, and Impression on Admission. A Consult(ant) Note, determined by a combination of site and worktype as listed in the document header, should have content in the sections identified as Consultants, and Impressions.

In some aspects of the invention, the database 102 supplies the discharge data to the assembly engine 108 on line 116, and the assembly engine 108 automatically generates the clinical summary in response to receiving the discharge date. Alternately, the discharge date trigger can be supplied to the assembly engine when the input information 122 is submitted. Further, the discharge data can be supplied from the converter 118 or parsing engine 112 (not shown).

The system 100 further comprises an validator 130 having an input connected to the output of the file converter on line 124. In general, the validator 130 accepts information and verifies that the information is correct, and if not, provides an option of correction. The validator 130 checks the converted input information for errors, inconsistent data, and incompletely entered data. The validator 130 has a first output connected to the parsing engine input on line 114 to supply accepted input information and a second output on line 132 to supply unaccepted input information with notated errors. The validator 130 has a second input on line 134 to accept correction procedures for the unaccepted input information selected from the group including permitting error overrides, correcting errors, returning the entered information for correction. The implementation of the above-mentioned correction procedures is represented by editor unit 136. Correction procedures can involve entries by a human operator or action by a software driven artificial intelligence, or combinations of software and human intervention. The validator 130 supplies the input information to the parsing engine 112 on line 114 after correction.

In one aspect of the invention, the input information is presented to a human user if any editing rules are violated. Only the patient's account number and the relevant data sections need to be edited in this view. The balance of the data can also be displayed for the user, as this is sometimes used to create the required section content. The viewer web page can be used having some functionality for database look-ups of patient account numbers by name based on corresponding ADT data objects. In case the content is created or modified by a user, some marker is inserted into the marked up information, such as an attribute marker, to distinguish a modified data object. Alternately, this information might be tracked separately by document id and element or content modified.

If the input information is accepted by the validator 130, the parsing engine 112 will store it in a table in database 102 as a text BLOB together with tagged data fields intended to help index and identify documents. In one aspect of the invention, the following fields will be pulled from a source document input information header, with some critical fields marked in boldface:

Patient name;
Patient MRN (medical record number);
Patient account number;
Site ID;
Worktype ID;
Job number;
Physician name;
Physician ID;
Transcriptionist ID;
Dictated Date; and
Created Date.

In some aspects of the invention, the validator 130 has a third input connected to the output of the assembly engine 108 on line 110 to check the clinical resume for errors, inconsistent data, and incompletely entered data. The validator 130 supplies accepted clinical resumes at a third output on line 138. Unaccepted clinical resumes with notated errors are supplied to the editor 136 at the second output on line 132. The second input (line 134) of the validator 130 accepts correction procedures selected from the group including permitting error overrides, correcting errors, returning the entered information for correction, and reentering the clinical resume after correction.

The validator 130 assesses document quality on a specific set of criteria. For example, the criteria can be tied to each of three document components: document fragments or physician transcriptions, coding data, and discharge instructions. If a document fails a criterion, the validator 130 checks the override settings supplied from editor 136 to determine if the document is acceptable in spite of the identified errors. If the document fails on a non-overridden criterion, it is not passed to the output stage on line 138, and an error row is written into the deficiency/error log stored in the database through communications on line 140. The deficiency/error log can be viewed through a basic web interface at editor 136 that permits an operator to override specific criteria for that individual document on reprocessing.

In addition to corrections, the parsing engine 112 accepts modifications to the originally entered input information 122, such as the coding data, descriptive information, laboratory results, pharmacy records, audio and graphical records, and physician transcriptions. The modifications are stored as data objects in the database 102, and the assembly engine 108 tracks the original and modified data objects.

The following is an example of a header and body section of a medical discharge summary such as might be generated by the present invention assembly engine 108.

---

Document Name:
Admit Date: 11/27/2000
Discharge Date: 12/01/2000
Patient Identification Number: 01234567
Patient Last Name, First Name: PATIENT, TEST
Account Number for Patient's Stay: 123456789012
Attending Physician's Name: PHYSICIAN, TEST
Attending Physician's Number: 1234
NAME: PATIENT, TEST
MRN: 01234567
Acct #: 123456789012
Att. Phy: PHYSICIAN, TEST
DATE OF ADMISSION: 11/27/2000
DATE OF DISCHARGE: 12/01/2000
DISCHARGE DIAGNOSES:

-continued

| | |
|---|---|
| 427.81 | Sinoatrial node dysfunction |
| V45.81 | Postsurgical aortocoronary bypass status |
| 437.1 | Other generalized ischemic cerebrovascular disease |
| 300.00 | Anxiety state, unspecified |
| 443.9 | Unspecified peripheral vascular disease |
| 427.31 | Atrial fibrillation |
| 427.89 | Other specified cardiac dysrhythmias |

REASON FOR ADMISSION:

Rule out cerebrovascular accident. Doubt myocardial infarction, as was the emergency room physician's impression.
IMPRESSION ON ADMISSION:

Confusion with disorientation, rule out cerebrovascular accident.
Atrial fibrillation with bradyarrhythmias and sick sinus syndrome.
Diabetes mellitus. Electrolyte imbalance.
CONSULTATION:

M.Y. PHYSICIAN, M.D., 11/29/2000. Patient with severe bradycardia and confusional state, who service has requested placement of a pacemaker. They are currently undergoing a workup, so this has to be determined whether or not she needs this for sure, but we will plan on placing this. We will keep her n.p.o. after midnight. We will check her coags and correct them down to at least 1.5 prior to any operative intervention. We will give her preoperative antibiotics.
PROCEDURES:

| | | |
|---|---|---|
| 20001130 | 99.07 | Transfusion of other serum |
| 20001130 | 37.83 | Initial insertion of dual-chamber device |
| 20001130 | 37.72 | Initial insertion of transvenous leads (electrodes) into atrium and ventricle |

HOSPITAL COURSE:
    If dictated: Date: _/_/___Job#___
DISCHARGE INSTRUCTIONS:
ACTIVITIES:
DIET:
MEDICATIONS:
APPOINTMENT:
CONDITION ON DISCHARGE:
Good__ Fair__ Serious__ Critical__ Expired__

Figure 2B:
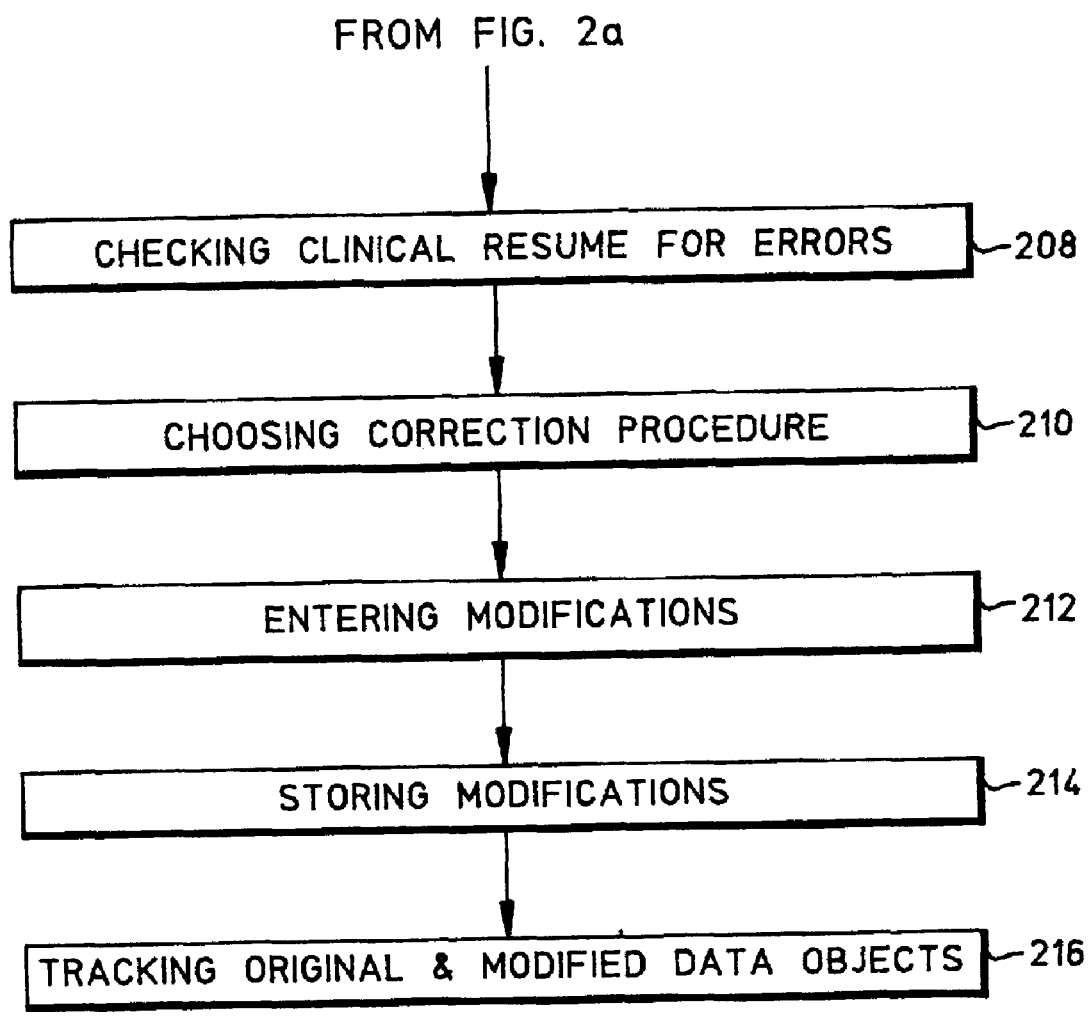

FIGS. 2a and 2b are a flowchart illustrating a method for creating a summary document according to the present invention. Although the process is depicted as a sequence of numbered steps for clarity, no order is to be inferred from the ordering unless explicitly stated. The method begins as Step 200. Step 202 stores data objects from a plurality of sources. Step 204 mines the data objects. Step 206 generates a summary document using the mined data objects. Mining data objects in Step 204 includes mining data objects that include marked up data, and generating a summary document using the mined data objects in Step 206 includes generating a summary document using the marked up data.

Typically, mining the data objects in Step 204 includes mining marked up data from the group including physician transcriptions, audio records, and graphical records. Then, generating a summary document using the mined data objects in Step 206 includes generating a clinical resume. Thus, when mining data objects in Step 204 includes mining data objects that include physician transcripts, generating a summary document using the mined data objects in Step 206 includes generating a clinical resume for the treatment of a first patient using the physician transcriptions.

Some aspects of the invention include further steps. Step 201a enters information including coding data, discharge instructions, laboratory results, pharmacy records, audio and graphical records, and physician transcriptions in an electronic format from a plurality of sources. Typically, entering physician transcriptions in Step 201a includes entering transcription sections concerning present illness, history of present illness, impressions on admission, impressions and plans on admission, admitting diagnosis, diagnosis on admission, consultation data, impression and plan from consultation, impression from consultation, and diagnosis from consultation information. Entering coding data, discharge instructions, laboratory results, and pharmacy records includes entering data selected from the group including patient identity fields, account number, worktype ID, job number, transcriptionist ID, dictation date, creation date, facility identity fields, physician identity fields, discharge diagnosis coding fields, procedure coding fields, discharge coding fields, laboratory result fields, audio and graphic recordings, and radiation result fields.

Step 201b marks up the coding data, discharge instructions, laboratory results, and pharmacy records as tagged data. Step 201c marks up the audio and graphical records, and physician transcriptions as marked up data. Typically, marking up the coding data, discharge instructions, laboratory results, and pharmacy records as tagged data in Step 210b, and the audio and graphical records, and physician transcriptions as marked up data in Step 201c includes marking up in accordance with a protocol selected from the group including HTML, XML, SGML, and equivalent protocols.

Step 201d parses the marked up data and tagged data into data objects. Then, storing data objects from a plurality of sources in Step 202 includes storing the marked up data and tagged data. In some aspects of the invention, depending on the type of data, storing the marked up data in Step 202 includes storing the marked up data as data BLOBs. Further, generating a summary document using the mined data objects in Step 206 includes generating a clinical resume for the treatment of a first patient using the marked up data and the tagged data.

In some aspects of the invention a further step, Step 203, triggers the creation of a clinical resume for the first patient. Then, generating a summary document using the mined data objects in Step 206 includes automatically generating a clinical resume within a first number of days of the triggering.

In some aspects of the invention, entering coding data, discharge instructions, laboratory results, pharmacy records, audio and graphic records, and physician transcriptions as information in an electronic format in Step 201 a includes entering the information in an untagged data format. Then, a further step, Step 201a1, converts the untagged data into a format suitable for marking up.

Some aspects of the invention include entering the admission and discharge dates, transfer information, and attending physician information as untagged data in an ADT file in Step 201a. The untagged data in the ADT file is converted to tagged data in Step 201a1. The ADT file is parsed into tagged data objects in Step 201b, and stored as tagged data objects of the ADT file in Step 202. In some aspects, entering the discharge date acts to trigger the creation of the clinical summary (Step 203).

Some aspects of the invention include further steps. Step 201c1, following the marking up the coding data, discharge instructions, laboratory results, and pharmacy records as tagged data in Step 201b, and the audio and graphical records, and physician transcriptions as marked up data in Step 210c, checks the data objects for errors, inconsistent data, and incompletely entered data. In response to checking the data objects, Step 201c2 chooses a correction procedure selected from the group including noting errors, permitting error overrides, returning the source document for correction, and re-parsing entered data after correction.

Likewise, following the generation of the clinical resume in Step 206, Step 208 checks the clinical resume for errors, inconsistent data, and incompletely entered data. In response to checking the clinical resume, Step 210 chooses a correction procedure selected from the group including permitting error overrides, returning the source document for correction, and re-parsing entered data after correction.

In some aspects of the invention, entering physician transcriptions in Step 201a includes entering transcriptions identified with a heading such as Reasons for Admission, Impression on Admission, and Consultations. Then, generating the clinical resume in Step 206 includes automatically generating a clinical resume with text sections including the transcribed Reasons for Admission texts, Impression on Admission texts, and Consultations.

Some aspects of the invention include further steps. Step 212, following the parsing of the marked up data and tagged data into data objects in Steps 201c and 201b, enters modifications and corrections to the originally entered coding data, descriptive information, laboratory results, pharmacy records, audio and graphical records, and physician transcriptions. Step 214 stores the modifications as data objects, and Step 216 tracks the original and modified data objects.

Figure 3:
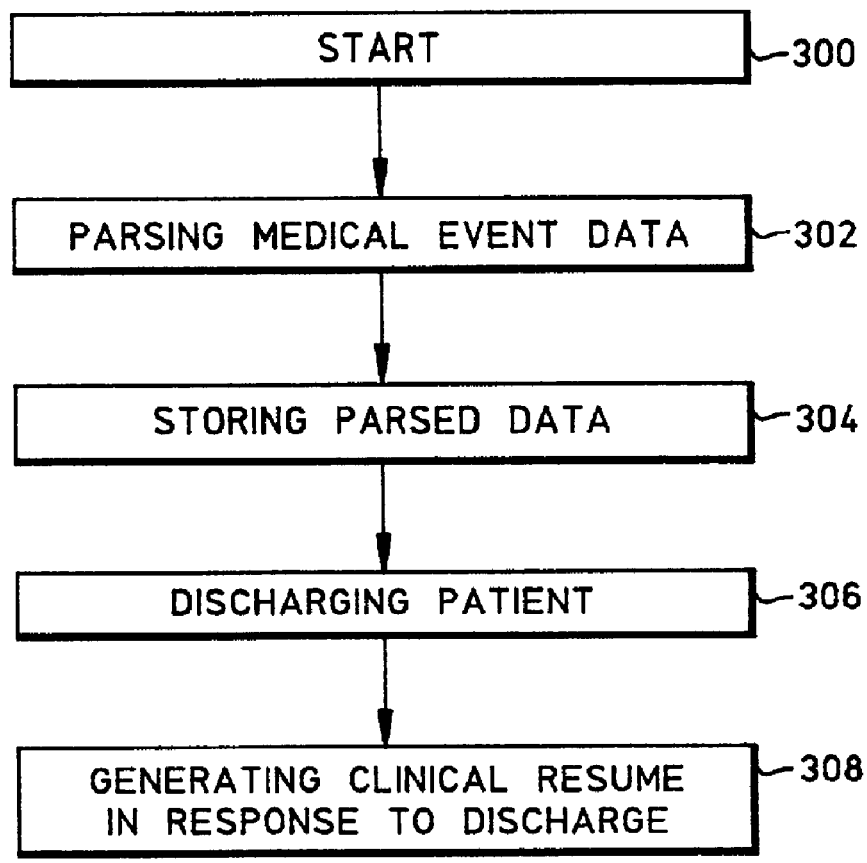
FIG. 3 is a flowchart illustrating a method for creating a clinical resume.

FIG. 3 is a flowchart illustrating a method for creating a clinical resume. The method begins at Step 300. Step 302 parses medical event data relating to a first patient. Step 304 stores the parsed medical event data. Step 306 discharges the first patient. Step 308, in response to discharging the first patient, automatically generates a clinical resume from the parsed medical event data in storage.

Figure 4:
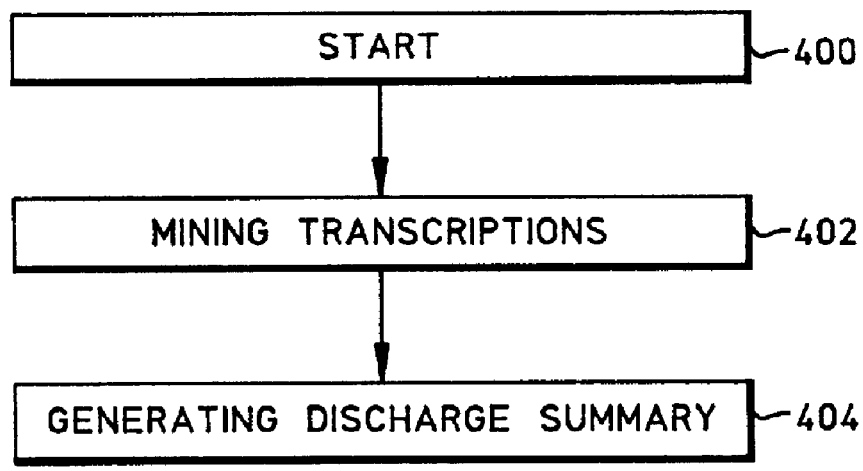
FIG. 4 is a flowchart illustrating a method for creating a medical discharge summary document.

FIG. 4 is a flowchart illustrating a method for creating a medical discharge summary document. The method begins at Step 400. Step 402 data mines a plurality of physician transcriptions that describe medical observations. Step 404 generates a medical discharge summary document from the medical observations.

A system and method have been presented above for generating a summary document from information mined from a plurality of data sources. Although specific examples have been given of mining marked up physician transcriptions, the invention can also be applied to the creation of documents that include audio and graphical sections. The above description should not be interpreted to mean that the output summary document created by the present invention can only be a hardcopy, the invention is equally applicable to electronically formatted summary documents. Further, although examples are provided of generating a clinical or medical document, the invention has broader applications. Other variations and embodiments of the invention will occur to those skilled in the art.

We claim:

1. A system for creating a summary document from stored data, the system comprising:
   a database having an input to accept information from a plurality of sources, store the information in an electronic format as data objects, and supply the data objects at an output;
   an assembly engine having a first input connected to the database output, a second input to accept a trigger signal for creating a clinical resume, and an output to supply a summary document generated by mining the data objects in the database, wherein the assembly engine generates the clinical resume from the mined data objects automatically within a first number of days of receiving the trigger signal;
   a file converter having an input to accept input information including coding data, discharge instructions, laboratory results, pharmacy records, audio and graphical records, and physician transcription information as untagged data, and an output connected to the input of the parsing engine to supply the input information in a format suitable for marking up;
   a validator having an input connected to the output of the file converter, the validator checking the converted input information for errors, including inconsistent data, and incompletely entered data, the validator having a first output connected to the parsing engine input to supply accepted input information and a second output to supply unaccepted input information with notated errors, the validator having a second input to accept correction procedures including permitting error overrides, correcting errors, returning the entered information for correction, and supplying the input information to the parsing engine after correction; and
   a parsing engine having an input to accept data and an output connected to the database input, the output supplying the coding data, discharge instructions, laboratory results, and pharmacy records as tagged data, and supplying the audio and graphical records, and the physician transcription information as marked up data, the physician transcription information including information concerning present illness, history of present illness, impressions on admission, impressions and plans on admission, admitting diagnosis, diagnosis on admission, consultation data, impression and plan at consultation, impression from consultation, and diagnosis from consultation;
   the parsing engine generating the marked up data according to a protocol selected from the group including HTML, XML, SGML, and equivalent protocols;
   wherein the database stores the tagged data and the marked up data as the data objects;
   wherein the file converter accepts patient admission, discharge date, transfer information, and attending physician information as untagged data in an ADT file and converts the ADT file into a format suitable for marking up;
   wherein the parsing engine marks up the untagged data in the converted ADT file;
   wherein the database accepts the tagged data and the marked up data from the parsing engine; and
   wherein the assembly engine generates the clinical resume with information including information mined from the ADT file.

2. The system of claim 1 wherein the validator has a third input connected to the output of the assembly engine to check the clinical resume for errors, inconsistent data, and incompletely entered data, the validator supplying accepted clinical resumes at a third output and unaccepted clinical resumes with notated errors the second output, and wherein the second input of the validator accepts correction procedures including permitting error overrides, correcting errors, returning the entered information for correction, and reentering the clinical resume after correction.

3. The system of claim 2 wherein the parsing engine accepts coding data, discharge instructions, laboratory results, and pharmacy records including patient identity fields, account number, worktype ID, job number, transcriptionist ID, dictation date, creation date, facility identity fields, physician identity fields, discharge diagnosis coding fields, procedure coding fields, discharge coding fields , laboratory result fields, and radiation result fields.

4. The system of claim 3 wherein the parsing engine marks and stores a plurality of physician transcriptions identified as Reasons for Admission, Impression on Admission, and Consultations; and wherein the assembly engine automatically generates a clinical resume with a plurality of Reasons for Admission, Impressions on Admission, and Consultations transcriptions mined from the database.

5. The system of claim 4 wherein the parsing engine accepts modifications and corrections to the originally entered coding data, descriptive information, laboratory results, pharmacy records, audio and graphical records, and physician transcriptions, an stores the modifications as data objects in the database; and wherein the assembly engine tracks the original and modified data objects.

6. The system of claim 1 wherein the database stores the up data objects as binary large objects (BLOBs).

7. The system of claim 1, wherein the database supplies the discharge date to the assembly engine; and wherein the assembly engine automatically generates the clinical resume in response to receiving the discharge date.

* * * * *